(12) United States Patent
Falke et al.

(10) Patent No.: US 10,197,514 B2
(45) Date of Patent: *Feb. 5, 2019

(54) MULTI-MODULE PHOTON DETECTOR AND USE THEREOF

(71) Applicant: Bruker Nano GmbH, Berlin (DE)

(72) Inventors: Meiken Falke, Jahnsdorf (DE); Waldemar Hahn, Berlin (DE)

(73) Assignee: Bruker Nano GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/712,712

(22) Filed: Sep. 22, 2017

(65) Prior Publication Data

US 2018/0038810 A1 Feb. 8, 2018

Related U.S. Application Data

(63) Continuation of application No. 14/415,405, filed as application No. PCT/EP2013/065092 on Jul. 17, 2013, now Pat. No. 9,797,848.

(30) Foreign Application Priority Data

Jul. 26, 2012 (DE) .......... 10 2012 213 130

(51) Int. Cl.
*G01T 1/24* (2006.01)
*H01J 37/244* (2006.01)
*G01N 23/2252* (2018.01)

(52) U.S. Cl.
CPC ......... *G01N 23/2252* (2013.01); *G01T 1/244* (2013.01); *H01J 37/244* (2013.01);
(Continued)

(58) Field of Classification Search
CPC ................................................. G01N 23/2252
See application file for complete search history.

(56) References Cited

U.S. PATENT DOCUMENTS 6,407,387 B1 * 6/2002 Frosien ........... H01J 37/28
250/310
8,080,791 B2 12/2011 von Harrach et al.
(Continued)

FOREIGN PATENT DOCUMENTS

DE 102008019406 A1 10/2009
DE 102008014578 B3 11/2009
(Continued)

OTHER PUBLICATIONS

Wiens et al, The AGATA triple cluster detector, Nuclear Instruments and Methods in Physics Research A, 618, 2010, 223-233.
(Continued)

*Primary Examiner* — David P Porta
*Assistant Examiner* — Jeremy S Valentiner
(74) *Attorney, Agent, or Firm* — Fox Rothschild LLP

(57) ABSTRACT

The invention relates to a photon detector (10), in particular an x-ray detector, in the form of a measurement finger, which extends along a detector axis (23) and has a detector head (11) at a first end of the measurement finger, wherein the detector head (11) comprises a plurality of at least two detector modules (22), each comprising a sensor chip (12) sensitive to photon radiation (14), in particular x-radiation, said sensor chip having an exposed end face (13) and a face facing away from the end face (13), wherein the detector modules (22) are arranged around the detector axis (23) in a plane (24) extending orthogonally to the detector axis (23).

12 Claims, 4 Drawing Sheets

(52) U.S. Cl.
CPC ............... *H01J 2237/2442* (2013.01); *H01J 2237/2445* (2013.01); *H01J 2237/2446* (2013.01); *H01J 2237/26* (2013.01)

(56) References Cited

U.S. PATENT DOCUMENTS

| | | |
|---|---|---|
| 2010/0133442 A1 | 6/2010 | Hansen et al. |
| 2010/0148064 A1* | 6/2010 | Harrach ............... H01J 37/244 250/307 |
| 2011/0204229 A1 | 8/2011 | Schamber |
| 2012/0132818 A1* | 5/2012 | Falke ................... H01J 37/244 250/370.01 |
| 2012/0228498 A1 | 9/2012 | Scheid et al. |

FOREIGN PATENT DOCUMENTS

| | | |
|---|---|---|
| DE | 102008028487 | 1/2010 |
| DE | 102009024928 A1 | 10/2010 |
| DE | 102009026946 A1 | 12/2010 |
| DE | 102010056321.8 | 6/2012 |
| JP | H07014538 A | 1/1995 |
| JP | H08222172 A | 8/1996 |
| JP | 11086783 | 3/1999 |
| JP | 2011524012 | 8/2011 |
| WO | WO 2010146044 A1 * 12/2010 ............ H01J 37/244 |

OTHER PUBLICATIONS

E. Gatti & P. Rehak: Nuclear Instruments and Methods in Physics Research 255:608-621, (1984).
L. Strueder et al.: Microscopy and Micro analytics 4, 622-631, (1999).
D. B. Williams et al.: Journal of Electron Microscopy 51 (Supplement): S113-S126 (2002).
H. Soltau et al.: Microsc. Microanal. 15 (Suppl. 2), (2009) Microscopy Society of America, 204-205.
International Search Report dated Oct. 21, 2013 in International Application No. PCT/EP2013/065092.

* cited by examiner

MULTI-MODULE PHOTON DETECTOR AND USE THEREOF

CROSS-REFERENCE TO RELATED APPLICATIONS

This application is a U.S. Continuation Application of U.S. application Ser. No. 14/415,405 filed on Jan. 16, 2015, which is a § 371 national stage entry of International Application No. PCT/EP2013/065092, filed Jul. 17, 2013, which claims priority to German Application No. 10 2012 213 130.2, filed Jul. 26, 2012, all of which are hereby incorporated herein by reference in their entireties.

The invention relates to a photon detector, in particular an X-ray detector, and its use for energy-dispersive X-ray detection within an electron microscope.

Electron microscopy, in which a sample is scanned with an electron beam, is used for spectroscopic and imaging material analysis of structures with sizes ranging from the visible to the atomic level. One method of analysing the sample material with regard to its individual periodic table elements is the detection of photons generated during electron microscopy in the material examined due to the electrons. The energy or wavelength of these photons is specific to the element in which they were generated and is located in the X-ray range. This method is called electron probe microanalysis and has in the meantime evolved into a routinely used method.

Figure 1:
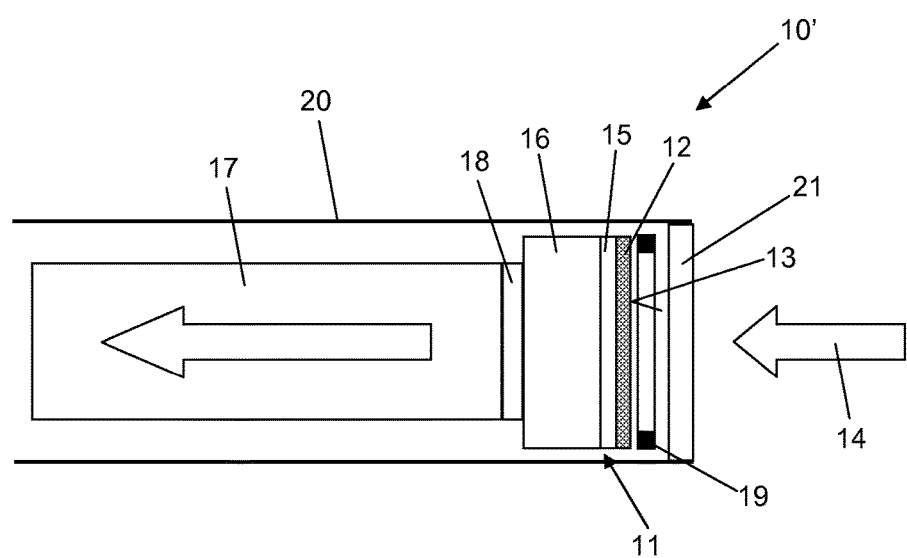

The crucial step toward the widespread application of electron probe microanalysis was the introduction of energy-dispersive X-ray detectors (EDX detectors), which are distinguished by their simple and robust design, low maintenance, stable operation and not least the relatively large solid angle that is captured. EDX detectors 10'—as shown in FIG. 1—usually (corresponding to the direction of the incoming radiation 14) have an active sensor chip 12 made of a semiconductor crystal with an end face 13 exposed to the radiation, a printed circuit board 15 connected to the sensor chip, an active or passive cooling means 16 and a means for heat removal 17. The combination of sensor chip 12, printed circuit board 15 and cooling means 16 forms the sensor head 11 which is soldered to the means for heat removal 17 via a solder connection 18. Also known in the art are solderless connections, which are usually bolted, glued or plug connections. In addition, X-ray detectors frequently have a collimator 19 for shielding against secondary X-radiation. The detector 10' can optionally be designed as a closed system, in which case it will have a housing 20 and an input window 21 arranged in front of the sensor chip 12.

The development of electron microscopes towards ever better resolution, the improvement in electron detectors, but also the increased interest in organic or otherwise sensitive samples have resulted in the standard beam current being lowered to the extent that in many cases there are distinct limits set even with EDX detectors. If the structural area of the sample material that is exposed to radiation becomes smaller, the number of photons generated becomes smaller as well, all other parameters being equal. The solid angle which can be captured for detecting the photons must therefore be as large as possible in order to detect a maximum amount of photons in a reasonable measurement time. To enlarge the solid angle, a distance between sample and detector that is as small as possible is aimed at, within a range of a few millimeters. This poses a problem because available electron microscopes usually do not provide much space around the sample examined.

The problem becomes particularly apparent in the case of so-called SDD detectors (silicon drift detectors), the physical mode of action and design of which means that they would be able to capture a much higher quantity of radiation than usual. SDD detectors comprise specially designed rigid silicon chips which will be hereinafter referred to as detector chips or sensor chips (E. Gatti & P. Rehak: Nuclear Instruments and Methods in Physics Research 255:608-621, (1984); L. Stüder et al.: Microscopy and Microanalytics 4, 622-631, (1999)). When the beam current is limited due to the sample or the appliance, the only way of increasing the captured quantity of radiation and hence reducing the measurement time is to enlarge the solid angle of radiation captured by the detector. For this purpose, it is desirable for the distance between the detector and the sample to be as small as possible.

Known from DE 10 2008 014 578 A is a magnetic trap for intercepting stray electrons in X-ray detectors which has small dimensions, allowing to build a smaller detector.

DE 10 2009 026 946 A describes a sensor head for an X-ray detector which is made of low-interference materials and thereby facilitates a closer proximity to the sample and thus a larger solid angle without interfering with the magnetic field that focuses the electron beam in the electron microscope.

Known in the art is furthermore a method of enlarging the solid angle captured and thus the quantity of photons detected by introducing several fully-fledged individual detectors from different sides into the pole shoe area near the sample (commercially available from the Bruker company; D. B. Williams et al.: Journal of Electron Microscopy 51 (Supplement): 5113-5126 (2002), JP 07-014538 A). This approach is also followed in U.S. Pat. No. 8,080,791 B2, where the detector chips are inserted directly into the pole shoe area of the electron microscope and signal processing means are arranged as individual components partially inside and partially outside the microscope. The use of several individual detectors, however, requires that several free adapter ports are available through which the measurement fingers of the detectors must be inserted into the microscope column. This requirement is often not fulfilled or only for a maximum of two or three ports. Furthermore, each measurement finger that is additionally inserted increases the amount of space required outside and around the microscope column. In order to insert active detector chips directly into the pole shoe area, as in U.S. Pat. No. 8,080,791 B2, a complex and expensive alteration or redesign of the microscope is required as well. Furthermore, the redesign of the pole shoe area requires practical know-how which only the microscope manufacturer, but not the detector supplier specialising in photon detectors and spectroscopy, possesses.

A different approach to enlarging the solid angle is based on the use of detectors with relatively large-surface sensor chips, said sensor chips having active surface areas of around 100 $mm^2$, for example (Jeol company). Large individual detector surfaces, however, have the disadvantage that the edge regions of the active detector surface directed towards the sample are further away from the photon source than the central area. This leads to detection losses in the edge regions and to inaccuracies regarding efficiency and energy resolution, since different angles of incidence of the beam and different sample-sensor distances have effects that are distributed over the large detector surface. In addition, detector chip surface areas larger than approximately 60 $mm^2$ require a higher cooling power for high-quality operation than small detector surface areas (ca. ≤60 $mm^2$), thus requiring an increased technical effort. It is also evident that large chip surfaces counteract an arrangement where the detector operates near the sample and that they, in particular, can not be moved as close to the sample as smaller active chip surfaces. The solid angle gain for large individual chip surfaces is therefore limited in comparison to smaller surfaces.

Also available are multi-segment chips which have multiple active segments on a single detector chip and can be built into measurement fingers (H. Soltau et al.: Microsc. Microanal. 15 (Suppl. 2), (2009) Microscopy Society of America, 204-205). The applications of such chips are limited, however, since their outer diameter determines the required measurement finger diameter. In addition, geometrical freedom is limited by the arrangement of the active chip segments on a plane (the silicon chip plane). There is also the previously mentioned problem that the edge regions of the individual chip segments have other geometrical conditions for detecting photons than the inner regions, which leads to inaccuracies.

It is therefore the object of the present invention to suggest a detector, in particular for EDX analysis in electron microscopes, that overcomes at least some of the problems known from the prior art. In particular, the detector should have high accuracy with regard to energy resolution and ideally cover a large solid angle while being constructed in a small and compact manner.

The problem is solved through a photon detector and its uses with the features of the independent claims. Further embodiments according to the present invention are the subject of the subclaims.

The photon detector according to the present invention has the shape of a measurement finger which extends longitudinally along a detector axis and has a detector head at a first end of the measurement finger. The detector head comprises a plurality of at least two detector modules, each at least comprising a sensor chip sensitive to photon radiation, said sensor chip having an exposed end face which therefore can be exposed to the radiation to be detected. The detector modules of the detector head are arranged around the detector axis in a plane extending orthogonally to the detector axis.

The detector according to the present invention thus has not a single detector module but a plurality of at least two detector modules or at least two sensor chips which are arranged preferably in a substantially circular manner around the detector axis substantially in the same plane oriented orthogonally to the detector axis. (The plane in which the detector modules are arranged therefore extends such that the detector axis is positioned orthogonally on the plane.) This arrangement results in several advantages. To start with, a plurality of relatively small active surfaces of the sensor chips of the individual detector modules leads to a homogenising of the incoming photon radiation with regard to its incidence angles and path lengths (distance between photon source and point of incidence on the chip). This means that the differences between the incidence angles and path lengths at the edge and central regions of the individual sensor chips are smaller, due to the smaller chip sizes, compared to a single larger sensor chip. This results in a higher energy resolution of the photon spectra, while detection losses in the edge regions as well as angles of beam incidence which vary too widely and thus result in inaccurate analysis and quantification are prevented. Furthermore, less heat is generated if the active surfaces of the sensor chips are smaller. The required individual cooling power thus can be reduced, which leads to better and more homogeneous cooling compared to a single, relatively large sensor chip. Finally, smaller sensor chips can be more cheaply manufactured than large ones.

In the context of the present application, a "measurement finger" is understood to be a substantially column-like, compact form which extends longitudinally and can be aligned with its first end into the direction of the photon source to be detected. The "viewing direction" of the detector therefore corresponds substantially to its detector axis. A cross-sectional area of the measurement finger (transverse to the detector axis) can be chosen arbitrarily; for example, it can be circular such that the measurement finger will have a substantially cylindrical shape, or it can be oval or quadrangular or similarly shaped.

The photon detector according to the present invention is preferably designed as an X-ray detector, wherein the sensor chips are sensitive to at least a partial spectral range of X-radiation. In particular, the photon detector is an energy-dispersive X-ray detector (EDX detector). The suitability for X-ray detection does, however, not prevent the detector from being sensitive to photons from other spectral ranges than the X-ray spectral range, as well. Although the present description, at least in part, makes specific reference to an X-ray detector and to X-radiation, it is to be understood that all explications also apply to detectors sensitive to other spectral ranges.

In a preferred embodiment of the invention, the detector modules have an axially symmetric arrangement relative to the detector axis. In the context of the present application, an "axially symmetric arrangement" is understood to be an arrangement where a rotation of the detector at discrete rotation angles about the detector axis results in the detector modules being mapped onto themselves. This applies in particular to rotation angles of 360°/n, with n being the number of detector modules. If there are 2 detector modules then the detector modules are mapped onto each other at a rotation angle of 180° about the detector axis, in the case of 3 detector modules at a rotation angle of 120°, in the case of 4 detector modules at a rotation angle of 90°, in the case of 5 detector modules at a rotation angle of 72°, in the case of 6 detector modules at a rotation angle of 60°, in the case of 7 detector modules at a rotation angle of approximately 52°, in the case of 8 detector modules at a rotation angle of 45°, etc.

An alternative definition consists of an arrangement of the detector modules around the detector axis such that they exhibit mirror symmetry with respect to a at least one mirror plane, wherein the mirror plane is in one plane with the detector axis. Provided that the detector is suitably oriented in a transmission electron microscope, this arrangement of a number of detector modules permits the recording of photons from the front and the back side of the sample (see below).

According to a particularly preferred embodiment of the present invention, at least a part of the sensor chips, preferably all of the sensor chips, are inclined relative to the plane extending orthogonally to the detector axis, in particular such that said sensor chips have an angle of inclination of <90° between the end face of the sensor chip and the detector axis in the viewing direction of the X-ray detector. This embodiment achieves an enlargement of the active surface area of the sensor chips and thus an enlargement of the solid angle captured. In addition, the inclined arrangement of the chips permits a further improvement with regard to an angle of incidence of the X-radiation captured that is uniform over the entire active individual detector surface, thereby making more precise quantification results possible.

Preferably, the sensor chips are arranged in an inclined manner such that their angle of inclination relative to the detector axis is within a range from 10° to <90°, in particular within a range from 20° to <80°, preferably within a range from 30° to 60°, particularly preferably of 45°. In this context, it is not required that all sensor chips are arranged at the same angle of inclination.

In a particularly preferable embodiment of the present invention, the sensor chips are arranged in an inclined manner such that the totality of their (generally planar) end faces approximates a spherical or paraboloidal arrangement or a section of such an arrangement. Preferably, the approximately spherical or paraboloidal surface area of the totality of end faces is aligned symmetrically about the detector axis and—in installed condition—thus symmetrically about an approximately punctiform source of radiation. In this way the solid angle captured is enlarged even more.

The number of detector modules can be chosen arbitrarily, e.g. 2, 3, 4, 5, 6, 7, 8, 9, 10, 11, 12 or more). Preferably, their number is 2 to 12, in particular 2 to 8, particularly preferably 2 to 4.

Preferably, each of the detector modules further comprises a printed circuit board which is arranged on the face of the sensor chip facing away from the end face and connected in a signal-conducting manner to the sensor chip. The printed circuit boards each have conductor tracks applied on top of a base plate, for example consisting of a ceramic or plastic material or a composite.

Photon sensors usually comprise cooling means for active (refrigerative) or passive (heat-dissipating) cooling of the sensor chip. In the context of a particularly preferred embodiment of the present invention, each of the detector modules comprises an active cooling element, each of which could be designed in particular as a thermoelectric cooling element (Peltier element) so that each individual detector module is individually cooled. This would achieve a particularly good cooling performance and hence a particularly good energy resolution. Alternatively, each of the detector modules further comprises a heat-conducting base, said heat-conducting bases of the detector modules being in thermal contact with a common means for heat removal of the detector (passive cooling). According to a further alternative embodiment of the invention, each of the detector modules further comprises a heat-conducting base, said heat-conducting bases of the detector modules being in thermal contact with a common active cooling element of the detector. It is evident that all aforementioned cooling means, whether active or passive, will be arranged on the face of the sensor chip facing away from the exposed end face or on the side of the printed circuit board facing away from the sensor chip. This means that they are arranged downstream of the sensor chips or the printed circuit boards with regard to a direction of incidence of the radiation. (In the context of the present application, the phrases "arranged upstream" and "arranged downstream" each refer on principle to the direction of incidence of a photon stream to be detected.)

According to a further embodiment, an additional (common) active cooling element can be arranged downstream of the aforementioned cooling means with regard to the direction of radiation incidence, or in other words, at a position located further back in the measurement finger. This possibility can be combined with each of the three aforementioned alternative cooling means. In the preferred case of having active cooling in each individual module, there are thus two active cooling means.

Both in the case of a common active cooling element and in the case of individual active cooling elements in the modules, and also if both variants are used concurrently, the cooling element or each of the cooling elements is preferably designed as a thermoelectric cooling element (Peltier element). Such elements are advantageous due to their small sizes and their easy controllability via the current flow. The heat-conducting base or bases for passive cooling comprise a heat-conducting material, meaning a material with a relatively high specific thermal conductivity such as copper.

Preferably, each of the detector modules further comprises a collimator arranged on the end face of the sensor chip, said collimator being employed to shield against secondary X-radiation induced by the primary photons of the sample examined once they strike other components. Substantially, the collimator is a geometric filter with an aperture function. As an alternative to having collimators in each individual module, the detector could also have just a single collimator.

Furthermore, the X-ray detector could also have a magnetic electron trap which intercepts stray electrons, especially if said X-ray detector is used in connection with a scanning electron microscope. The electron trap is arranged on or in front of the end faces of the sensor chips. Advantageously, the electron trap can be designed in accordance with DE 10 2008 014 578 A.

The end faces (active surfaces) of the sensor chips can be of the same size or of different sizes. In particular, the sensor chips independently of each other have an end face within a range from 2 mm$^2$ to 100 mm$^2$, preferably within a range from 10 mm$^2$ to 80 mm$^2$, particularly preferably within a range from 20 mm$^2$ to 50 mm$^2$. The individual sensor chips preferably have end faces of equal size.

Similarly, the outlines of the end faces of the sensor chips may be either the same or different, but preferably the outlines are the same. The outline depends primarily on the number of detector modules and the outer shape of the measurement finger and is preferably selected such that the entire available surface of the "viewing face" of the detector is used, if possible. For example, the sensor chips could independently of each other have a circular, oval, triangular, quadrangular or hexagonal outline or the outline of a sector or a segment of a circle. Outlines with angular elements can also be rounded, making it possible, for example, to use a drop-shaped outline (rounded outline of a sector of a circle) as well.

According to a further advantageous embodiment of the invention, each of the detector modules further comprises a collimator which is arranged upstream of the sensor chip (in each individual module). Alternatively the photon detector comprises a common collimator arranged upstream of all detector modules. In a further alternative embodiment, the detector comprises at least one common collimator arranged upstream of a subgroup of detector modules.

Furthermore, the detector can also be designed as a closed system and have a casing (housing) as well as a window or several windows made of a material permeable to radiation, in particular X-radiation. This embodiment serves to protect the sensor chips. The alternative embodiments mentioned in connection with the collimator apply here as well. Each of the detector modules can therefore further comprise a window arranged upstream of the sensor chip (in each individual module). Alternatively, all detector modules could be protected by a single common window, or groups of individual modules could be protected individually by their own separate windows.

If the detector has a window or several windows and a collimator or several collimators, the collimator or collimators are preferably arranged upstream of the window or windows. In this case the collimator is therefore arranged at the outside.

The sensor chips are preferably designed as silicon drift detectors (SDD).

A further aspect of the present invention relates to the use of the X-ray detector according to the invention for energy-dispersive X-ray detection (EDX) within an electron microscope (scanning electron microscope (SEM) or transmission electron microscope (TEM)).

In a preferred embodiment, in particular in the case of an X-ray detector with sensor chips arranged in an inclined manner, said detector can be arranged within a TEM such that its detector axis is located substantially in the sample plane. This arrangement permits the detection of both the X-radiation originating from the front side of the sample irradiated by the electron beam and the radiation originating from the back side of the sample.

Figure 2:
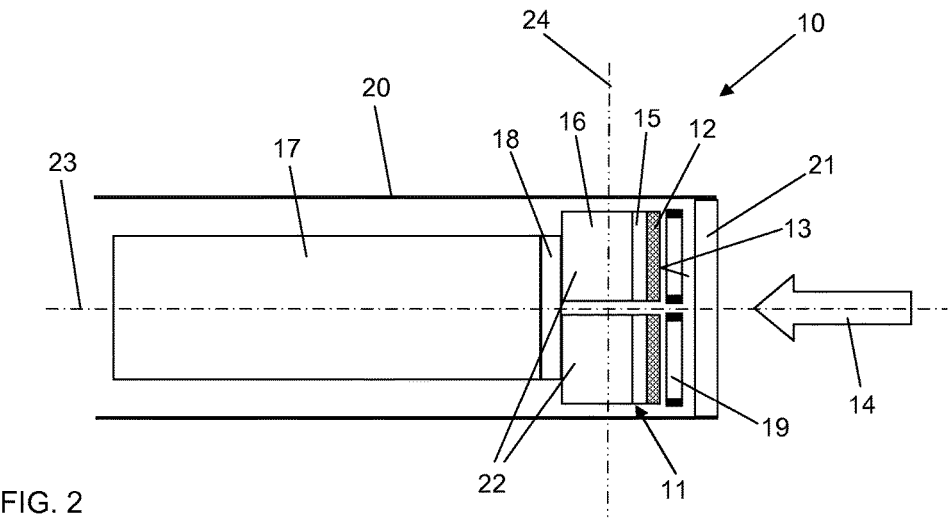
Figure 3:
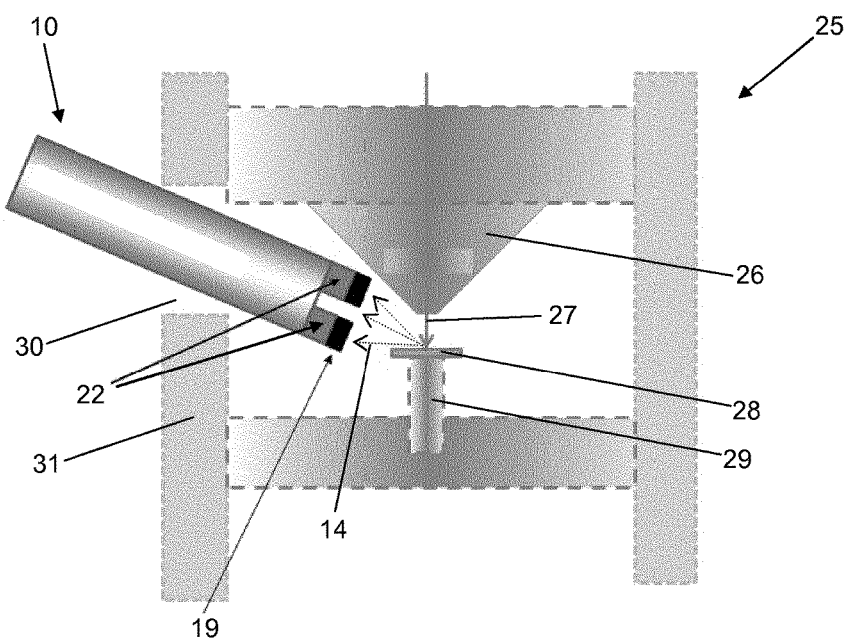
Figure 4:
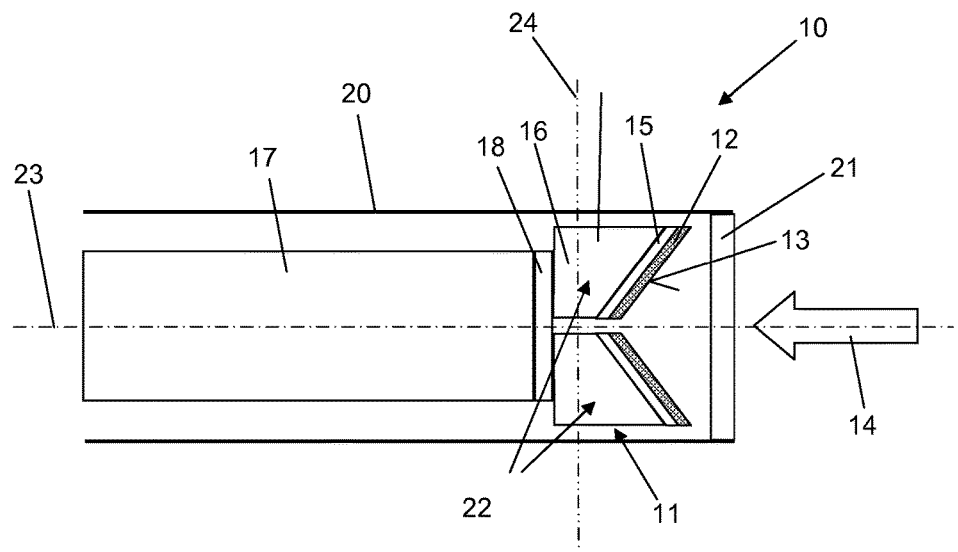
Figure 5:
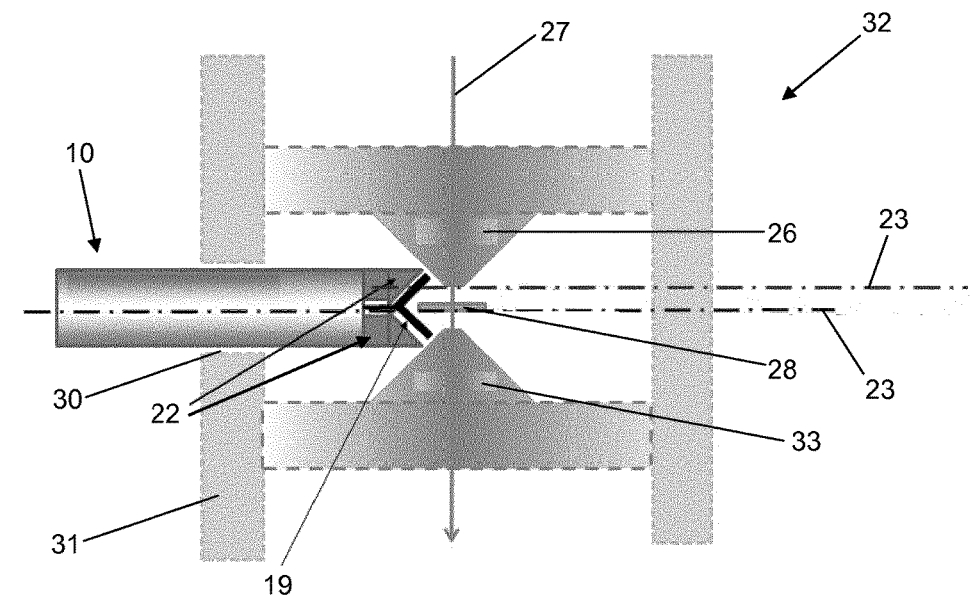
Figure 6:
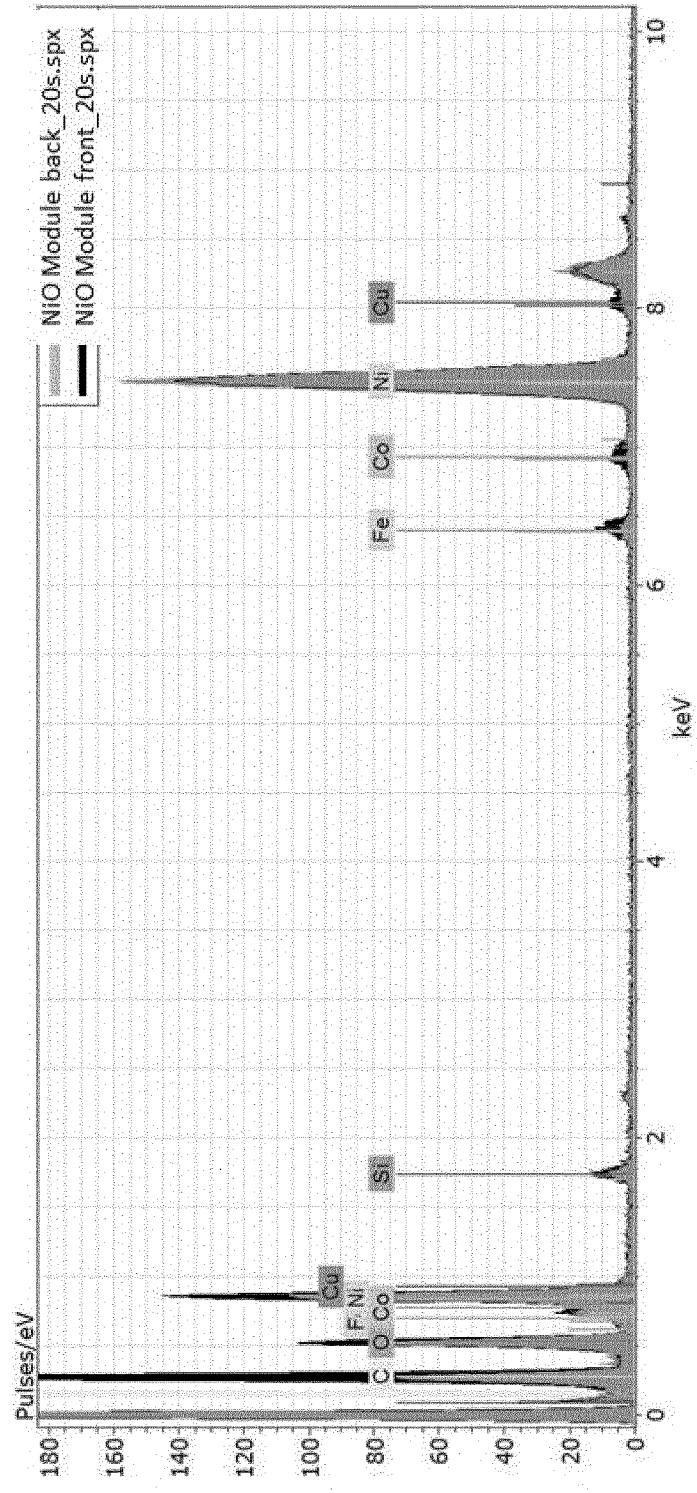

In the following, the invention will be explained in detail using some embodiments and the accompanying drawings. The figures show:

FIG. 1 an X-ray detector in accordance with the state of the art in a sectional view;

FIG. 2 an X-ray detector in accordance with the present invention in a first embodiment in a sectional view;

FIG. 3 an arrangement of an X-ray detector according to FIG. 2 within a scanning electron microscope (SEM);

FIG. 4 an X-ray detector in accordance with the present invention in a second embodiment in a sectional view;

FIG. 5 an arrangement of an X-ray detector according to FIG. 4 within a transmission electron microscope (TEM) and FIG. 6 an example of a photon spectrum recorded using an arrangement according to FIG. 5.

The following description relates to an X-ray detector, specifically an energy-dispersive X-ray detector (EDX detector). It is to be understood, however, that all explications also apply to detectors sensitive to other spectral ranges.

The fundamental design of an X-ray detector 10' in accordance with the state of the art according to FIG. 1 has already been presented in the introduction.

FIG. 2 shows an X-ray detector 10 according to a first embodiment of the present invention.

The core element of the detector 10 is a sensor head 11 arranged at a front end of the detector. The sensor head 11 according to the present invention has a plurality of detector modules 22. In the given example there are four detector modules 22, of which only two are visible in the selected representation. Each individual detector module 22 comprises a sensor chip 12, which is a semiconductor element sensitive to X-radiation that is preferably designed as a silicon drift detector (SDD). The end faces 13 (also referred to as active surfaces) of the sensor chips 12 are exposed such that they can be exposed to photon radiation, in particular X-radiation, indicated as 14. Each of the detector modules 22 further comprises a printed circuit board 15 which is arranged on a face of the sensor chip 12 facing away from the end face 13, said printed circuit board having a signal-conducting connection to the respective sensor chip 12. The printed circuit board has bonding islands connected via bonding wires to contact connections for the purpose of transmitting the recorded signals (bonding islands, bonding wires and contact connections not shown here). To achieve a miniaturization of the X-ray detector, the printed circuit boards and the so-called bonding can be designed advantageously in accordance with DE 10 2008 028 487 A. The bonding is preferably applied only on two opposite sides of the printed circuit board.

According to the example shown, each detector module 22 further comprises a cooling element 16 for individual active cooling of the sensor chips 12, said cooling element being arranged on the side of the printed circuit board 15 facing away from the sensor chip 12. The cooling elements 16 are preferably designed as thermoelectric cooling elements (Peltier elements).

The sensor chip 12, the printed circuit board 15 and the cooling element 16 can further be mounted on a bottom plate that is not shown.

The modules 22 forming the sensor head 11 are tightly bolted, plugged in or soldered via a solder connection 18 to the means for heat removal 17, in particular via the base of said modules which is not shown. The means for heat removal 17 comprises a heat-conducting material such as copper or is built as a so-called heat pipe and serves substantially to remove heat (passive cooling element).

A collimator 19 can be optionally arranged in front of the sensor chip 12, said collimator shielding the sensor chip 12 from secondary photons. In addition, a magnetic electron trap can be optionally arranged in front of the sensor head 11, said magnetic electron trap shielding from stray electrons of the electron microscope. The magnetic electron trap can be advantageously designed in accordance with DE 10 2008 014 578 A.

If the X-ray detector 10 is not designed as an open system but—as illustrated—as a closed system, the aforementioned components can be enclosed by a housing 20 which has a window 21 permeable to X-radiation located at its front end. Alternatively, the individual modules could also be protected by individual windows.

In a preferred embodiment of the present invention, the detector 10 can be made of materials selected from low-interference materials in accordance with DE 10 2009 026 946 A, in particular from materials with a magnetic permeability value $\mu_r$ that is smaller than 1.5. This could apply in particular to the materials used for the contact pins, the bottom plate, the housing 20, the window 21, any adhesive and barrier layers used and the solder connection 18. Suitable materials are designated in the aforementioned publication.

It is furthermore possible to have the detector designed such that it not only detects photon radiation, in particular X-radiation, but also electrons. Such a detector is described in DE 10 2009 024 928 A.

The detector 10 has the shape of a measurement finger which extends longitudinally along a detector axis 23. The detector modules 22 are arranged in a plane 24 on which the detector axis 23 is positioned orthogonally. According to the representation selected in FIG. 2, the plane 24 extends perpendicular to the paper plane. The detector modules 22 preferably have an axially symmetric arrangement relative to the detector axis 23. Therefore they have at least one mirror plane in which the axis 23 is located such that the detector modules 22 are mapped onto themselves if mirrored about the mirror plane.

In the example shown, four sensor chips 12, each with a circular outline (in the view of the photon beam 14), are arranged in a square. However, other outlines can also be used in the context of the present invention.

For further signal processing the detector 10 is equipped with or connected to an amplifier unit that is not shown, said amplifier unit typically having a field-effect transistor (FET)

and a preamplifier. The signals recorded with such a detector are used in a spectrometer for further processing into photon spectra. The photon spectra can be measured location-dependently using electron beam scanning in an electron microscope. This is facilitated by imaging, meaning location-dependent, element analysis.

FIG. 3 shows an exemplary arrangement of a detector as illustrated in FIG. 2 within a scanning electron microscope (SEM) 25. The SEM 25 comprises a pole shoe 26 from which a focused electron beam 27 emanates. The electron beam 27 hits the sample to be examined, said sample being held on a sample holder 28 which is arranged on a sample bench 29. The electron beam 27 excites the sample material, resulting in X-radiation 14 being emitted by the sample into all spatial directions. A part of the X-radiation 14 hits the X-ray detector 10 which is installed in a port 30 of a microscope wall 31 of the SEM 25. Here the X-ray detector 10 is arranged such that all sensor chips 12 of the detector modules 22 are facing the front side of the sample irradiated by the electron beam 27.

It must be taken into account that the size of the detector 10 in FIG. 3 is not to scale relative to the electron microscope 25. Instead, the size of the detector 10 is shown exaggerated. Furthermore, the optional housing 20 and the optional window 21 are omitted in FIG. 3.

FIG. 4 shows an X-ray detector 10 according to a further embodiment of the present invention. Matching elements have the same reference symbols and—unless indicated otherwise—the same properties as in FIG. 2.

While the sensor chips 12 of the X-ray detector shown in FIG. 2 are arranged orthogonally to the detector axis 23, the sensor chips 12 of the X-ray detector 10 according to FIG. 4 have an inclined arrangement relative to the detector axis 23 or the plane 24. In the example shown, the angle of inclination between the end face 13 of the sensor chip 12 and the detector axis 23 is uniformly 45°. However, deviations are possible where the angles of inclination of the individual sensor chips 12 differ from each other or where one part of the sensor chips is arranged orthogonally according to FIG. 2 and another part of the sensor chips is in an inclined arrangement according to FIG. 4.

Preferably, the sensor chips 12 are inclined and aligned symmetrically about the detector axis 23 or the X-radiation 14 such that the totality of their individual end faces 13 approximates a spheroid or paraboloid.

FIG. 4 shows no collimators; however, such collimators can be optionally present, either in the form of one individual collimator for each of the detector modules 22 or as a single common collimator or as one or more collimators for one or several of the modules.

FIG. 5 shows the arrangement of the sensor according to FIG. 4 in a transmission electron microscope (TEM) 32 (the relative sizes are again not to scale). Here, unlike in FIG. 4, the housing 20 and the window 21 of the detector 10 are not shown; shown, however, are two collimators 19 for the individual modules.

Apart from its upper pole shoe 26, the TEM 32 also has a lower pole shoe 33, with the sample holder 28 being arranged between the two pole shoes 26 and 33. The electron beam 27 traverses through the sample and exits through the lower pole shoe 33 for further electron microscopic analysis.

According to FIG. 5, the X-ray detector 10 is arranged within the TEM 32 such that its detector axis 23 is substantially in the plane of the sample held on the sample holder 28. In this manner not only the X-radiation originating from the front side of the sample irradiated by the electron beam 27 but also the X-radiation originating from the back side of the sample can be recorded. A further advantage of this arrangement is that no active sensor surface is present in the plane of the sample where the X-radiation that has been altered only by the sample holder and the bulk portions of the sample and interferes with the measurement is emitted. Instead, the detector 10 has a gap between the detector modules 22 in this plane. Since the unwanted radiation components can be kept away from the active sensor chip surfaces in this manner, an improved signal-to-noise ratio results.

Deviating from the arrangement illustrated in FIG. 5, the X-ray detector 10 according to the present invention can also be arranged within a transmission electron microscope such that it is exclusively located on the side of the sample facing the electron beam 27 or exclusively located on the side of the sample facing away from the electron beam 27.

The embodiment of the X-ray detector according to the present invention with at least two detector modules 22 facilitates different approaches to reading out and further processing of the signals recorded. According to a first option, the signals recorded by all modules 22 can be read out jointly in the form of mixed signals. Alternatively it is possible to read out the signals recorded by each module individually, which can be done either at the same time (in parallel) or one after the other (sequentially). In the case of more than two detector modules 22, the signals recorded by any combination of two or more modules 22 can be read out jointly in aggregate form, which again can be done either at the same time (in parallel) or one after the other (serialised).

The detector according to FIG. 4 has been tested in a transmission electron microscope using an arrangement according to FIG. 5. During the test, the signals recorded by the detector module 22 arranged on the side of the sample facing the electron beam 27 were evaluated separately from the signals recorded by the module 22 arranged on the side of the sample facing away from the electron beam 27. FIG. 6 shows the energy-dispersive X-ray photon spectra obtained in this manner. There the X-ray spectrum recorded at the front side of the sample appears in black and the spectrum recorded at the back side of the sample in grey.

It can be seen that in particular the background radiation recorded in the low-energy range at the back side of the sample (grey) forms a larger part of the spectrum, as was to be expected, than at the front side of the sample (black). When measuring at the side of the sample facing the electron beam, the element sensitivity, meaning the peak-to-background ratio, is better than at the back side of the sample, in particular in the low-energy range. It can also be seen that more scattered radiation due to backscattered electrons hitting the upper pole shoe of the microscope is recorded at the side of the sample facing the electron beam, leading to the occurrence of peaks of the materials iron (Fe) and cobalt (Co) of the pole shoe.

REFERENCE SYMBOL LIST

10' X-ray detector in accordance with the state of the art
10 X-ray detector in accordance with the invention
11 sensor head
12 sensor chip
13 end face
14 photon beam/X-ray beam
15 printed circuit board
16 cooling element
17 means for heat removal
18 solder connection
19 collimator 20 housing
21 window
22 detector module
23 detector axis
24 plane
25 scanning electron microscope
26 pole shoe
27 electron beam
28 sample holder
29 sample bench
30 port
31 microscope wall
32 transmission electron microscope
33 pole shoe

The invention claimed is:

1. A photon detector (10), having the form of a column-like measurement finger which extends longitudinally along a detector axis (23), the photon detector comprising:
   a detector head (11) provided at a first end of the measurement finger, wherein the detector head (11) comprises a plurality of at least two detector modules (22), the detector modules (22) being arranged around the detector axis (23) in a plane (24) extending orthogonally to the detector axis (23), and
   a housing (20) having the form of a column extending longitudinally along the detector axis (23), the housing (20) accommodating the detector head (11) including the at least two detector modules (22);
   each detector module (22), individually and separately comprising:
      a sensor chip (12) sensitive to photon radiation (14), said sensor chip having an exposed end face (13),
      a printed circuit board (15) which is arranged on the face of the sensor chip (12) facing away from the end face (13) and connected in a signal-conducting manner to the sensor chip (12), and
   at least one of an active cooling element (16) and a heat-conducting base, said heat-conducting bases being in thermal contact with a common means for heat removal of the detector (10) or with a common active cooling element of the detector (10).

2. The photon detector (10) according to claim 1, wherein the detector modules (22) have an axially symmetric arrangement relative to the detector axis (23).

3. The photon detector (10) according to claim 1, wherein at least a part of the sensor chips (12) being inclined relative to the plane (24) extending orthogonally to the detector axis (23).

4. The photon detector (10) according to claim 3, wherein an angle of inclination of the sensor chips (12) is within a range from 10 degrees (10°) to less than 90 degrees (90°) between the end face (13) of the sensor chip (12) and the detector axis (23).

5. The photon detector (10) of claim 1, wherein the number of detector modules (22) is 2 to 12.

6. The photon detector (10) of claim 1, wherein the active cooling element (16) is a thermoelectric cooling element.

7. The photon detector (10) of claim 1, further comprising at least one collimator (19) arranged upstream of the individual sensor chips (12) or arranged upstream of all said sensor chips.

8. The photon detector (10) of claim 1, further comprising at least one window (21) arranged upstream of the individual detector modules (22) or arranged upstream of all said detector modules, said window being permeable to the photon radiation (14).

9. The photon detector (10) of claim 1, wherein the sensor chips (12) are formed as silicon drift detectors (SDD).

10. The photon detector (10) of claim 1, wherein the end faces (13) of the sensor chips (12) independently of each other have a surface area within a range from 2 mm$^2$ to 100 mm$^2$.

11. A use of a photon detector (10) according to claim 1 for energy-dispersive X-ray detection (EDX) within an electron microscope (25, 32).

12. The use according to claim 11, wherein the electron microscope is a transmission electron microscope (32) and the X-ray detector (10) is arranged with its detector axis (23) substantially in a sample plane.

* * * * *